United States Patent [19]

Shore et al.

[11] 4,389,347

[45] Jun. 21, 1983

[54] SYNTHESIS OF HETERONUCLEAR TRI-OSMIUM CARBONYL HYDRIDES UNDER GASEOUS HYDROGEN

[75] Inventors: Sheldon G. Shore; Wen-Liang Hsu, both of Columbus, Ohio

[73] Assignee: The Ohio State University Research Foundation, Columbus, Ohio

[21] Appl. No.: 322,447

[22] Filed: Nov. 18, 1981

[51] Int. Cl.$^3$ .................. C07F 11/00; C07F 15/02; C07F 15/04; C07F 15/06

[52] U.S. Cl. .................. 260/429 CY; 260/439 CY; 423/417

[58] Field of Search ..... 260/429 R, 439 CY, 429 CY; 423/417

[56] References Cited

U.S. PATENT DOCUMENTS

| | | | |
|---|---|---|---|
| 2,985,504 | 5/1961 | Orchin | 423/417 |
| 3,006,940 | 10/1961 | Fischer et al. | 260/429 CY |
| 3,236,597 | 2/1966 | Knap | 423/417 |
| 3,505,034 | 4/1970 | L'Eplattenier et al. | 260/429 R |
| 3,597,461 | 8/1971 | L'Eplattenier et al. | 260/429 R |
| 4,282,197 | 8/1981 | Shore et al. | 423/417 |
| 4,349,521 | 9/1982 | Shore et al. | 423/417 |
| 4,349,522 | 9/1982 | Shore et al. | 423/417 |

OTHER PUBLICATIONS

Moss et al., J. Organometal Chem. 23, C23–C24 (1970).
Geoffroy et al., JACS. 99, pp. 7565–7573, (1977).
Churchhill et al., J. Chem. Comm., p. 534, (1978).

Primary Examiner—Helen M. S. Sneed
Attorney, Agent, or Firm—Millard & Cox

[57] ABSTRACT

A process for producing a tri-osmium heteronuclear metal carbonyl compound comprises establishing a reaction mixture comprising an electron deficient cobalt, nickel, iron, molybdenum or rhodium carbonyl, $H_2Os_3(CO)_{10}$ and a solvent in the presence of gaseous hydrogen and recovering the tri-osmium heteronuclear metal carbonyl compound from the reaction mixture. Some of the cobalt, molybdenum and rhodium carbonyls produced are new.

40 Claims, No Drawings

SYNTHESIS OF HETERONUCLEAR TRI-OSMIUM CARBONYL HYDRIDES UNDER GASEOUS HYDROGEN

The Government has rights in this invention pursuant to Grant CHE-79-18148 awarded by the National Science Foundation.

BACKGROUND OF THE INVENTION

In the copending patent application, Ser. No. 06/275,693 filed June 22, 1981, which has one inventor (Sheldon G. Shore) in common with this application and which is assigned to the same Assignee as this application (the disclosure of the aforementioned application Ser. No. 06/275,693 being incorporated herein by reference), the prior art relating to the reactions of $H_2Os_3(CO)_{10}$ is reviewed. This prior art indicates that $H_2Os_3(CO)_{10}$ normally reacts as a Lewis acid.

The aforementioned application Ser. No. 06/273,693 demonstrates for the first time that $H_2Os_3(CO)_{10}$ also possesses apparent Lewis base character and discloses a process for making a tri-osmium heteronuclear metal carbonyl compound which comprises establishing a reaction mixture comprising an electron deficient cobalt, nickel or iron carbonyl or a cobalt, nickel or iron carbonyl anion, $H_2Os_3(CO)_{10}$, and a solvent which at least partially solubilizes at least one of the electron deficient carbonyl compound and the $H_2Os_3(CO)_{10}$, the $H_2Os_3(CO)_{10}$ reacting with the electron deficient carbonyl compound as a Lewis base, and recovering the tri-osmium heteronuclear metal carbonyl compound from the reaction mixture. Among the specific examples of this process described in detail in the aforementioned application are the reaction of $Co_2(CO)_8$ and $H_2Os_3(CO)_{10}$ to produce a major proportion of $HCoOs_3(CO)_{13}$ and a minor proportion of $H_3CoOs_3(CO)_{12}$, and the reaction of $[(\eta^5-C_5H_5)Ni(CO)]_2$ with $H_2Os_3(CO)_{10}$ to produce $H_3(\eta^5-C_5H_5)NiOs_3(CO)_9$. The yield of $H_3CoOs_3(CO)_{12}$ in the first of these two reactions is only about 5%, while the yield of $H_3(\eta^5-C_5H_5)NiOs_3(CO)_9$ in the second reaction is about 50%.

We have now discovered that, by carrying out the reaction described in the aforementioned application using the electron deficient carbonyl in the presence of gaseous hydrogen, the yields of certain of the tri-osmium nuclear metal carbonyl compounds produced can be markedly increased, and new carbonyls produced. In the case of the reactions described in the aforementioned application which produce a mixture of two products, the ratios between the two products can be shifted dramatically, so much so that in some cases what was formerly the minor product of the reaction becomes the only detectable product thereof. Furthermore we have also found that, by carrying out the reaction in the presence of hydrogen, carbonyls of metals other than cobalt, nickel or iron may be employed in the reaction.

SUMMARY OF THE INVENTION

Accordingly, the invention provides a process for producing a tri-osmium heteronuclear metal carbonyl compound, which comprises establishing, in the presence of gaseous hydrogen, a reaction mixture comprising an electron deficient cobalt, nickel, iron, molybdenum or rhodium carbonyl, $H_2Os_3(CO)_{10}$ and a solvent which at least partially solubilizes at least one of the electron deficient carbonyl compound and the $H_2Os_3(CO)_{10}$, and recovering the tri-osmium heteronuclear metal carbonyl compound from the reaction mixture.

In the instant process, the contact between the gaseous hydrogen and the reactants may be commenced either before or after the reaction mixture itself is established. Thus, the reactants may be mixed together to form the reaction mixture under an atmosphere of gaseous hydrogen, or the reaction mixture may be first formed and only thereafter subjected to gaseous hydrogen. In practice, it is usually more convenient to form the reaction mixture and then to begin the passage of hydrogen therethrough; to ensure proper contact between the gaseous hydrogen and the liquid reaction mixture, preferably the hydrogen is bubbled through the reaction mixture.

The term "electron deficient metal carbonyl" as used herein includes not only those carbonyls which are truly electron deficient but also those carbonyls which are not electron deficient in the normal sense but which will disproportionate to yield an electron deficient disproportionation product, such as $Fe_2(CO)_9$, which disproportionates to yield $Fe(CO)_5$ and electron-deficient $Fe(CO)_4$.

The solvent used in the instant process is desirably one which solubilizes both the electron deficient carbonyl and the $H_2Os_3(CO)_{10}$.

Preferred solvents for use in the instant process are aromatic solvents, ether solvents and chlorohydrocarbon solvents, the exact choice of solvents depending of course on the particular electron deficient carbonyl compound being used. Preferably the molar ratio of the electron deficient carbonyl compound to the $H_2Os_3(CO)_{10}$ is at least about stoichiometric. The electron deficient carbonyl compound may, if desired, be generated in situ in the reaction mixture for reaction with the $H_2Os_3(CO)_{10}$.

Many of the tri-osmium heteronuclear complexes produced by the instant process are sensitive to molecular oxygen and/or water. Accordingly, in most cases it is desirable to establish the reaction mixture in the substantial absence of molecular oxygen and water, usually under an inert gas blanket.

Examples of reaction which may be conducted by the instant process are as follows:

| | Electron deficient carbonyl compound | Heteronuclear tri-osmium product(s) |
| --- | --- | --- |
| A | $Co_2(CO)_8$ | $H_3CoOs_3(CO)_{12}$. |
| B | $[(\eta^5-C_5H_5)Ni(CO)]_2$ | $H_3(\eta^5-C_5H_5)NiOs_3(CO)_9$** |
| C | $[(\eta^5-C_5H_5)Mo(CO)_3]_2$ | $H_3(\eta^5-C_5H_5)MoOs_3(CO)_{12}$ |
| | | $H(\eta^5-C_5H_5)MoOs_3(CO)_{14}$* |
| | | $H_3(\eta^5-C_5H_5)MoOs_3(CO)_{11}$ |
| D | $(\eta^5-C_5H_5)Co(CO)_2$ | $H_2(\eta^5-C_5H_5)CoOs_3(CO)_{10}$** |
| | | $H_3(\eta^5-C_5H_5)CoOs_3(CO)_9$* |
| | | $H_4(\eta^5-C_5H_5)CoOs_3(CO)_9$* |
| E | $(\eta^5-C_5H_5)Rh(CO)_2$ | $H_2(\eta^5-C_5H_5)RhOs_3(CO)_{10}$* |

The two compounds in the above table marked with a double asterisk (**) are claimed in the aforementioned co-pending application Ser. No. 06/275,693. The compounds marked with a single asterisk (*) are novel and this invention extends to these novel compounds per se.

Preferred conditions for each of the specific reactions tabulated above will now be discussed, the reactions being identified by the electron deficient starting material:

A. $Co_2(CO)_8$

The solvent used in the reaction mixture is conveniently a chlorohydrocarbon, preferably methylene chloride. It is preferred to use at least one mole of $Co_2(CO)_8$ per mole of $H_2Os_3(CO)_{10}$ though more of the cobalt compound may be used if desired. The reaction mixture is desirably maintained at a temperature not above about room temperature (room temperature being defined for present purposes as 25° C.), room temperature being the preferred temperature for carrying out the reaction. The reaction mixture should desirably be established in the substantial absence of molecular oxygen and water.

After completion of the reaction, a substantial amount of $Co_4(CO)_{12}$ is present in the reaction mixture. To separate this by-product from the desired $H_3CoOs_3(CO)_{12}$, the reaction mixture is preferably chromatographed on silica gel using a hexane/benzene liquid phase.

B. $[(\eta^5\text{-}C_5H_5)Ni(CO)]_2$

The solvent used in the reaction mixture is conveniently an aromatic solvent, preferably toluene. It is preferred to use at least one mole of $[(\eta^5\text{-}C_5H_5)Ni(CO)]_2$ per mole of $H_2Os_3(CO)_{10}$, though more of the nickel compound may be used if desired. The reaction mixture is desirably maintained at a temperature in the range of about 80° to about 120° C., and preferably at about 90° C.

As disclosed in the aforementioned copending application Ser. No. 06/275,693, when the reaction of $[(\eta^5\text{-}C_5H_5)Ni(CO)]_2$ with $H_2Os_3(CO)_{10}$ is carried out in the absence of hydrogen, the reaction produces not only $H_3(\eta^5\text{-}C_5H_5)NiOs_3(CO)_9$ but also a minor but substantial proportion of a by-product which displays no hydride resonances in its proton nuclear magnetic resonance spectrum. Carrying out the reaction in the presence of hydrogen increases the yield of $H_3(\eta^5\text{-}C_5H_5)NiOs_3(CO)_9$ to about 93% based upon the $H_2Os_3(CO)_{10}$ used. No substantial amount of the non-hydride by-product is formed, so that purification of the product is simplified.

The reaction is preferably carried out in the substantial absence of molecular oxygen and water.

C. $[(\eta^5\text{-}C_5H_5)Mo(CO)_3]_2$

The solvent used in the reaction mixture is conveniently an aromatic solvent, preferably toluene. It is preferred to use at least one mole of $[(\eta^5\text{-}C_5H_5)Mo(CO)_3]_2$ per mole of of $H_2Os_3(CO)_{10}$, and indeed it is preferred to use the two reactants in substantially equimolar quantities. The reaction mixture is desirably maintained at a temperature in the range of about 80° to about 120° C., and preferably at about 90° C. The reaction mixture should desirably be established in the substantial absence of molecular oxygen and water.

As noted above, the reaction produces three separate products, namely $H_3(\eta^5\text{-}C_5H_5)MoOs_3(CO)_{12}$, $H(\eta^5\text{-}C_5H_5)MoOs_3(CO)_{14}$ and $H_3(\eta^5\text{-}C_5H_5)MoOs_3(CO)_{11}$. Separation of the products is conveniently effected by chromatography on silica gel, a convenient eluant being a 1:4 v/v benzene/hexane mixture.

D. $(\eta^5\text{-}C_5H_5)Co(CO)_2$

The solvent used in the reaction mixture is conveniently an aromatic solvent, preferably toluene. It is preferred to use more than one mole of $H_2(\eta^5\text{-}C_5H_5)CoOs_3(CO)_{10}$ per mole of $H_2Os_3(CO)_{10}$, and indeed in view of the relative cost of the two reactants, it is convenient to use approximately five moles of the cobalt compound per mole of the osmium compound. The reaction mixture is desirably maintained to a temperature in the range of about 80° to about 120° C., and preferably at about 90° C. The reaction mixture desirably is established in the substantial absence of molecular oxygen and water.

Separation of the three products of the reaction may conveniently be separated by chromatography under the same conditions described above with respect to reaction C.

E. $(\eta^5\text{-}C_5H_5)Rh(CO)_2$

The solvent used in the reaction mixture is conveniently an aromatic solvent, preferably toluene. It is preferred to use more than one mole of $(\eta^5\text{-}C_5H_5)Rh(CO)_2$ per mole of $H_2Os_3(CO)_{10}$, and indeed preferably about five moles of the rhodium compound are used per mole of the osmium compound. The reaction mixture is desirably maintained at a temperature in the range of about 80° to about 120°, and preferably at about 90° C. The reaction mixture should desirably be established in the substantial absence of molecular oxygen and water.

The products of the reaction are conveniently separated by chromatography in substantially the same manner as described for the products of reaction C above.

The instant process is not restricted to the specific reactions A-E described in detail above, but may be used for insertion of other transition metals into the tri-osmium framework. Such other pathways would involve the reaction of $H_2Os_3(CO)_{10}$ with an electron deficient (electrophilic) metal complex or intermediate complex. Such a system relies on the apparent Lewis base property or nucleophilicity of the tri-osmium cluster for synthesizing new heteronuclear metal clusters. While any transition metal could form the electron deficient metal complex, cobalt, nickel, molybdenum and rhodium are preferred as the metal of the electron deficient complex. Similarly, such electron deficient species need not be carbonyl complexes, but carbonyl complexes are preferred. Suitable solvents would be those solvents disclosed herein which solubilize at least one of the electron deficient metal complex and the tri-osmium reactant. It must be recognized that for each system the reaction conditions (e.g. temperature, molar ratio of reactants, tolerance of water, tolerance of molecular oxygen, etc.) may vary somewhat, but determination of such reaction conditions will be routine based on the disclosure herein contained.

In view of the proven ability of $H_2Os_3(CO)_{10}$ and $Os_3(CO)_{12}$ to catalyze olefin isomerizations, the mixed-metal clusters produced by the instant process are expected to have potential catalytic activity. Such clusters may perhaps be chemically attached to supports to provide a heterogeneous catalyst system analagous to the systems described by Pierantozzi et al., JACS, 101;18, 5436-5438 (1979). Moreover, such supported mixed-metal cluster compounds may have further utility by their reduction on the support to produce new bi-metallic cluster candidates having unique surface properties. Further information on such surface properties can be found in McVicker and Vannice, "The Preparation, Characterization and Use of Supported Potassium-group VIII Metal Complexes as Catalysts for CO Hydrogenation," Exxon Research and Engineering Company, Corporate Pioneering Research Laboratories, Linden, New Jersey (1979). Further data on transition metal carbonyl cluster catalyts is disclosed in Basset and Smith, Abstracts of Invited Talks, XIX, International Conference on Pure and Applied Chemistry, Prague, Czechoslovakia, pages 161-164 (1978). For a good discussion on cluster catalysis, reference is made to J. J. Bassett and R. Ugo, Aspects of Homogeneous Catalysis, Chapter 2, Vol. 3, D. Ridel, Dordrecht, Holland, (1977). In particular, the heteronuclear tri-osmium complexes produced by the instant method are believed to be useful as Fischer-Tropsch catalysts.

Examples of the instant process will now be given, by way of illustration only.

EXAMPLE 1

Preparation of $H_3CoOs_3(CO)_{12}$ from $Co_2(CO)_8$ 60 mg. of $H_2Os_3(CO)_{10}$ (0.07 mmol.) and 26 mg. of $Co_2(CO)_8$ (0.07 mmol.) were placed in a 50 ml. three-necked flask equipped with a condenser. Approximately 20 ml. of anhydrous methylene chloride (distilled from phosphorous pentoxide) were then condensed into the flask at $-78°$ C. After degassing by two freeze-pump-thaw cycles, the resultant reaction mixture was warmed to room temperature and magnetically stirred at this temperature for 24 hours while gaseous hydrogen was slowly bubbled through the solution. After the 24 hours stirring, a spot test by thin-layer chromatography indicated that complete consumption of the $H_2Os_3(CO)_{10}$.

The methylene chloride and a small remaining amount of $Co_2(CO)_8$ were removed from the reaction mixture under vacuum to leave a brownish yellow residue. This residue was dissolved in a 1-1 v/v benzene/hexane mixture and chromatographed on a silica gel column. Elution with hexane gave a dark brown band, identified by infrared spectroscopy as consisting of $Co_4(CO)_{12}$ and a small amount of $H_2Os_3(CO)_{12}$. A yellow band that remained at the top of the column was eluted with a 1:1 v/v benzene/hexane mixture and the solvent was removed in a rotary evaporator to leave 41 mg. of the orange-yellow product, $H_3CoOs_3(CO)_{12}$ (60% yield based on the $H_2Os_3(CO)_{10}$ starting material, identical to that produced as a by-product in the process described in Example 5 of the aforementioned copending application Ser. No. 06/275,693. The infrared spectrum in cyclohexane showed carbonyl bands at 2078(vs), 2062(m,sh), 2048(w), 2030(vs), 2025(vs), 2005(m), 1998(w,sh), 1980(vw). The known spectrum from the literature is 2076(vs), 2066(ms), 2049(w), 2030(vs), 2025(vs), 2012(w), 2005(s), 2000(sh) and 1982(w). The proton magnetic resonance spectrum in deuterochloroform showed a single peak at $\delta = -19.03$ ppm., the literature value of this compound in methylene chloride being $\delta = -19.1$ ppm.

EXAMPLE 2

Preparation of $H_3(\eta^5-C_5H_5)NiOs_3(CO)_9$ from $[(\eta^5-C_5H_5)Ni(CO)]_2$ 60 mg. of $H_2Os_3(CO)_{10}$ (0.07 mmol.) and 21 mg. of $[(\eta^5-C_5H_5)Ni(CO)]_2$ (0.07 mmol.) were placed in a 50 ml. three-necked flask equipped with a condensor. Approximately 20 ml. of anhydrous toluene was condensed at $-78°$ C. into the flask. After degassing two freeze-pump-thaw cycles, the resultant reaction mixture was warmed to 90° C. and magnetically stirred at this temperature for 10 hours while gaseous hydrogen was slowly bubbled through the solution. At the end of this 10 hours stirring, the infrared spectrum of a sample of the reaction mixture indicated the complete consumption of the $H_2Os_3(CO)_{10}$ since $H_3(\eta^5-C_5H_5)NiOs_3(CO)_9$ was the only species other than the solvent observable in the infrared spectrum. The toluene was removed from the reaction mixture in a rotary evaporator under reduced pressure to leave a purple residue which was purified by chromatography on a silica gel column using a 1:4 v/v benzene/hexane mixture as eluant. After removal of the benzene/hexane solvent, the resultant residue was recrystallized from methylene chloride/benzene to give 62 mg. of dark purple, crystalline $H_3(\eta^5-C_5H_5)NiOs_3(CO)_9$ (93% based on $H_2Os_3(CO)_{10}$), identical to the product produced in Example 6 of the aforementioned copending application Ser. No. 06/275,693.

EXAMPLE 3

Preparation of $H_3(\eta^5-C_5H_5)MoOs_3(CO)_{12}$, $H(\eta^5-C_5H_5)MoOs_3(CO)_{14}$, and $H_3(\eta^5-C_5H_5)MoOs_3(CO)_{11}$ from $[(\eta^5-C_5H_5)Mo(CO)_3]_2$ 150 mg. of $H_2Os_3(CO)_{10}$ (0.176 mmol.) and 87 mg. of $[(\eta^5-C_5H_5)Mo(CO)_3]_2$ (0.176 mmol.) were placed in a 50 ml. three-necked flask equipped with a condenser and maintained under a nitrogen atmosphere. Approximately 20 ml. of freshly distilled and degassed toluene was added to the flask. Pre-purified hydrogen gas was slowly bubbled through the reaction mixture, which was heated to 90° C. and maintained at this temperature, under stirring, for six days. At the end of the six-day reaction period, a spot test of the reaction mixture by thin layer chromatography indicated complete consumption of the $H_2Os_3(CO)_{10}$. Accordingly, the reaction mixture was cooled to room temperature and the toluene removed under reduced pressure on a rotary evaporator to leave a brownish residue.

This residue was dissolved in 5 ml. of methylene chloride and subjected to thin layer chromatography on silica gel (grade EM-60-F-254, the silica gel layer being 0.5 mm. in thickness) using a 1:4 v/v benzene/hexane mixture as the eluant. This chromatographic separation produced four bands; in order of decreasing $R_f$ values, the bands were yellow, pink, orange and reddish-brown. All four bands were separately scraped off the chromatography plate and eluted from the silica gel with methylene chloride. The methylene chloride was removed in a rotary evaporator and, except for the pink residue (which was found to be unchanged $[(\eta^5-C_5H_5)Mo(CO)_3]_2$), the separated residues were weighed and their high-resolution mass spectra, infrared spectra and proton magnetic resonance spectra recorded.

The yellow band yielded 18 mg. (6.4% based on the $H_2Os_3(CO)_{10}$) of $H(\eta^5-C_5H_5)MoOs_3(CO)_{14}$. The mass spectrum of this compound showed a parent peak at m/e = 1132, consistant with $^1H_6{}^{12}C_{19}{}^{16}O_{14}{}^{98}Mo{}^{192}Os_3$. The infared spectrum in cyclohexane showed bands at 2072(s), 2058 (vs), 2048(s), 2028 (m), 2018 (s), 2008 (m) and 1990 (w,sh) cm$^{-1}$. The proton magnetic resonance spectrum in dueterochloroform showed a singlet at $\delta = 5.28$ (5H), and a singlet at $\delta = -20.51$ (1H).

The orange band produced 20 mg. (11% based on the $H_2Os(CO)_{10}$ of $H_3(\eta^5-C_5H_5)MoOs_3(CO)_{11}$. The mass spectrum of this compound showed a parent peak at m/e = 1050, consistent with $^1H_8{}^{12}C_{16}{}^{16}O_{11}{}^{98}Mo{}^{192}Os_3$. The infrared spectrum in cyclohexane showed peaks at 2082(m), 2052 (s), 2046 (vs), 2008 (m), 1999 (m), 1962 (w) and 1953 (s) cm$^{-1}$. The proton magnetic resonance spectrum in deuterochloroform showed singlets at $\delta = 5.26$ (5H) and $-19.57$ (3H).

Finally the reddish-brown band produced 12 mg. (9% based on the $H_2Os_3(CO)_{10}$) of $H_3(\eta^5-C_5H_5)MoOs_3$-

$(CO)_{12}$. The infrared spectrum of this compound in hexane showed peaks at 2079 (vw), 2068 (w), 2042 (vs), 2023 (s), 1995 (s), 1986 (m), 1960 (vw), 1945 (vw) and 1842 (w) cm$^{-1}$. The proton magnetic resonance spectrum in deuterochloroform showed singlets at $\delta=5.56$ (5H) and $-18.16$ (1H) at room temperature.

Both $H_3(\eta^5\text{-}C_5H_5)MoOs_3(CO)_{11}$ and $H_3(\eta^5\text{-}C_5H_5)MoOs_3(CO)_{12}$ have been previously reported in the literature, but no spectral data have been given. See M. R. Churchill, F. J. Hollander, J. R. Shapley and D. S. Foose, J.Chem. Comm (1978), page 534.

EXAMPLE 4

Preparation of $H_3(\eta^5\text{-}C_5H_5)CoOs_3(CO)_9$, $H_4(\eta^5\text{-}C_5H_5)CoOs_3(CO)_9$ and $H_2(\eta^5\text{-}C_5H_5)CoOs_3(CO)_{10}$ from $(\eta^5\text{-}C_5H_5)Co(CO)_2$ 150 mg. of $H_2Os_3(CO)_{10}$ (0.176 mmol.) and 167 mg. of $(\eta^5\text{-}C_5H_5)Co(CO)_2$ (0.88 mmol.) were placed in a 50 ml. three-necked flask equipped with a condenser and maintained under a nitrogen atmosphere. Approximately 20 ml. of freshly distilled and degassed toluene was added to the flask. Pre-purified hydrogen gas was slowly bubbled through the resultant mixture, which was heated to 90° C. and kept at this temperature for 53 hours with stirring. At the end of this reaction period, the infrared spectrum of a sample of the reaction mixture indicated complete consumption of the $H_2Os_3(CO)_{10}$. Accordingly, the reaction mixture was cooled to room temperature and the toluene and the unconsumed cobalt carbonyl were removed under vacuum to leave a dark brown residue, which was dissolved in about 5 ml. of methylene chloride and subjected to thin layer chromatography using the same technique as in Example 3 except that preparative plates having a 2.0 mm. layer of silica gel were employed. The chromatogram showed three distinct bands, these being, in descending order of $R_f$ values, purple, dark green and green. The three bands were separately scraped off the plate, eluted with methylene chloride and the solvent removed in exactly the same manner as in Example 3.

The green band having the smallest $R_f$ produced 7.2 mg. (4% based on the $H_2Os_3(CO)_{10}$) of $H_2(\eta^5\text{-}C_5H_5)CoOs_3(CO)_{10}$ identical to the product produced in Example 3 of the aforementioned application Ser. No. 06/275,693.

The purple band produced 55 mg. (33% based on the $H_2Os_3(CO)_{10}$) of $H_3(\eta^5\text{-}C_5H_5)CoOs_3(C0)_9$. A high-resolution mass spectrum of this compound showed a parent peak at m/e=954.8369, consistent with $^{12}C_{14}{}^1H_8O_9{}^{59}Co^{192}Os_3$ (the theoretical molecular weight is 954.8336). The infrared spectrum of this compound in hexane showed peaks at 2082 (w), 2060 (s), 2008 (vs), 1990 (m) and 1955 (vw) cm$^{-1}$.

The dark green band produced 53 mg. (32% based on the $H_2Os_3(CO)_{10}$) of $H_4(\eta^5\text{-}C_5H_5)CoOs_3(CO)_9$. The high-resolution mass spectrum of this compound showed a parent peak at m/e=955.8387, consistent with $^{12}C_{14}{}^1H_9{}^{16}O_9{}^{59}Co^{192}Os_3$ (the theoretical molecular weight is 955.8415). The infrared spectrum of this compound in hexane showed peaks at 2082 (m), 2060 (s), 2050 (s), 2010 (s), 1995 (s,sh), 1992 (s), 1977 (m) and 1952 (vw) cm$^{-1}$. At room temperature the proton magnetic resonance spectrum of this compound in deuterochloroform showed singlets at $\delta=5.22$ (5H) and $-19.30$ (4H) ppm. At $-60°$ C., the singlet at $\delta=5.22$ was unchanged, but the singlet $\delta=-19.30$ was resolved into two singlets at $-18.26$ (2H) and 20.27 (2H) ppm. The $^{13}C$ proton-coupled nuclear magnetic resonance spectrum in methylene chloride at room temperature showed peaks at 79.7 ($J_{C-H}=180.4$ Hz, attributed to cyclopentadibenyl carbons), 171.2 (attributed to equatorial terminal carbonyls) and 176.8 (attributed to axial terminal carbonyls) ppm.

Based upon the foregoing spectral data, it is believed (though the invention is in no way limited by this belief) that the structure of $H_3(\eta^5\text{-}C_5H_5)CoOs_3(CO)_9$ is that of a tetrahedron of metal atoms, the cyclopentadienyl ligand being coordinated with the cobalt atom, three carbonyls being coordinated with each of the osmium atoms, and each of the Os-Os edges of the tetrahedron being bridged by a single hydrogen atom. In the compound $H_4(\eta^5\text{-}C_5H_5)CoOs_3(CO)_9$, the disposition of the cobalt, osmiums, carbonyls and cyclopentadienyl is similar but only two of the Os-Os edges are bridged by hydrogen atoms, the other two hydrogen atoms bridging the Os-Co edges of that face of the tetrahedron whose Os-Os edge is not bridged by a hydrogen atom.

A further experiment showed that the compound produced in the above experiment could be substantially completely converted to $H_4(\eta^5\text{-}C_5H_5)CoOs_3(CO)_9$ by slowly bubbling pre-purified hydrogen through a solution of the starting material in toluene at a temperature of 90° C. for 48 hours.

EXAMPLE RhOs$_3$ 5

Preparation of $H_2(\eta^5\text{-}C_5H_5)\text{-}RhOs_3(CO)_{10}$; from $(\eta^5\text{-}C_5H_5)Rh(CO)_2$ 150 mg. of $H_2Os_3(CO)_{10}$ (0.176 mmol.) and 196 mg. of $(\eta^5\text{-}C_5H_5)Rh(CO)_2$ (0.88 mmol.) were placed in a 50 ml. three-necked flask equipped with a condenser and maintained under a nitrogen atmosphere. Approximately 20 ml. of freshly distilled and degassed toluene was added to the flask. Pre-purified hydrogen gas was slowly bubbled through the resultant reaction mixture which was heated to 90° C. and maintained at this temperature for 72 hours with stirring. At the end of this reaction period, the infrared spectrum of a sample of the reaction mixture indicated the complete consumption of the $H_2Os_3(CO)_{10}$. Accordingly, the reaction mixture was cooled to room temperature and the toluene removed under vaccum to leave a reddish-brown oil, which was redissolved in 5 ml. of methylene chloride and subjected to thin-layer chromatography under the same conditions as in Example 4. The resultant chromatogram showed three bands, these being, in order of decreasing $R_f$ values, orange, greenish-brown and brown. These three bands were separately scraped off the plate, eluted with methylene chloride and the solvent removed by rotary evaporation. The brown band produced 14 mg. of an unidentified brown solid.

The orange band produced 45 mg. (26% based on the $H_3Os_3(CO)_9$) of an orange-red compound. The infrared spectrum of this compound in hexane showed peaks at 2070 (w), 2046 (s), 2000 (vs) 1984 (m) and 1950 (vw) cm$^{-1}$.

The greenish-brown band produced 15 mg. (8% based on the $H_2Os_3(CO)_{10}$ of greenish-brown $H_2(\eta^5\text{-}C_5H_5)RhOs_3(CO)_{10}$. The infrared spectrum of this compound in cyclohexane showed peaks at 2083 (m), 2063 (vs), 2042 (vs), 2010 (vs), 2000 (s,sh), 1982 (m), 1970 (m) and 1819 (m) cm$^{-1}$.

It will be apparent to those skilled in the art that numerous modifications and variations can be made in the preferred processes of the invention described above. Accordingly, the foregoing description is to be construed in an illustrative and not a limitative sense, the scope of the invention being defined solely by the appended claims.

We claim:

1. A process for producing a tri-osmium heteronuclear metal carbonyl compound, which comprises establishing, in the presence of gaseous hydrogen, a reaction mixture comprising an electron deficient cobalt, nickel, iron, molybdenum or rhodium carbonyl, $H_2Os_3(CO)_{10}$ and a solvent which at least partially solubilizes at least one of said electron deficient carbonyl and said $H_2Os_3(CO)_{10}$, said reaction mixture being established in the substantial absence of molecular oxygen and water, and recovering said tri-osmium heteronuclear metal carbonyl compound from said reaction mixture.

2. A process according to claim 1 wherein said electron deficient carbonyl is a cobalt, nickel, molybdenum or rhodium carbonyl.

3. A process according to claim 1 wherein said solvent solubilizes both said electron deficient carbonyl and said $H_2Os_3(CO)_{10}$.

4. A process according to claim 1 wherein said solvent is an ether solvent, and aromatic solvent or a chlorohydrocarbon solvent.

5. A process according to claim 4 wherein said solvent is toluene or methylene chloride.

6. A process according to claim 1 wherein the molar ratio of said electron deficient carbonyl to said $H_2Os_3(CO)_{10}$ is at least about stoichiometric.

7. A process according to claim 1 wherein said electron deficient carbonyl is generated in situ in said reaction mixture.

8. A process according to claim 1 wherein said gaseous hydrogen is bubbled through said reaction mixture.

9. A process according to claim 2 wherein said electron deficient carbonyl is $Co_2(CO)_8$ and said tri-osmium heteronuclear metal carbonyl produced is $H_3CoOs_3(CO)_{12}$.

10. A process according to claim 9 wherein said reaction mixture comprises said $Co_2(CO)_8$ and said $H_2Os_3(CO)_{10}$ in a molar ratio of at least about 1:1 and a non-polar solvent in which said cobalt and tri-osmium compounds are soluble, said reaction mixture being established at a temperature not above about room temperature and said gaseous hydrogen being bubbled through said reaction mixture.

11. A process according to claim 10 wherein said solvent is a chlorohydrocarbon.

12. A process according to claim 11 wherein said solvent is methylene chloride.

13. A process according to claim 10 wherein said reaction mixture is chromatographed on silica gel using a hexane/benzene liquid phase to separate said $H_3CoOs_3(CO)_{12}$ from $Co_4(CO)_{12}$ by-product.

14. A process according to claim 2 wherein said electron deficient carbonyl is $[(\eta^5-C_5H_5)Ni(CO)]_2$ and said tri-osmium heteronuclear metal carbonyl produced is $H_3(\eta^5-C_5H_5)NiOs_3(CO)_9$.

15. A process according to claim 14, wherein said reaction mixture comprises said $[(\eta^5-C_5H_5)Ni(CO)]_2$ and said $H_2Os_3(CO)_{10}$ in a molar ratio of at least about 1:1 and a non-polar solvent in which said nickel and tri-osmium compounds are soluble, said reaction mixture being established at a temperature in the range of about 80° to about 120° C. and said gaseous hydrogen being bubbled through said reaction mixture.

16. A process according to claim 15 wherein said solvent is an aromatic solvent.

17. A process according to claim 16 wherein said solvent is toluene.

18. A process according to claim 15 wherein said reaction mixture is established at a temperature of about 90° C.

19. A process according to claim 2 wherein said electron deficient carbonyl is $[(\eta^5-C_5H_5)Mo(CO)_3]_2$ and said tri-osmium heteronuclear metal carbonyl compound produced comprises at least one of $H_3(\eta^5-C_5H_5)MoOs_3(CO)_{12}$, $H(\eta^5-C_5H_5)MoOs_3(CO)_{14}$ and $H_3(\eta^5-C_5H_5)MoOs_3(CO)_{11}$.

20. A process according to claim 19 wherein said reaction mixture comprises said $[(\eta^5-C_5H_5)Mo(CO)_3]_2$ and said $H_2Os_3(CO)_{10}$ in a molar ratio of at least about 1:1 and a non-polar solvent in which said molybdenum and tri-osmium compounds are soluble, said reaction mixture being established at a temperature in the range of about 80° to about 120° C. and said gaseous hydrogen being bubbled through said reaction mixture.

21. A process according to claim 20 wherein said solvent is an aromatic solvent.

22. A process according to claim 21 wherein said solvent is toluene.

23. A process according to claim 20 wherein said reaction mixture is established at a temperature of about 90° C.

24. A process according to claim 20 wherein said reaction mixture is chromatographed on silica gel using a hexane-benzene liquid phase to separate the products of said reaction.

25. A process according to claim 2 wherein said electron deficient carbonyl wherein $(\eta^5-C_5H_5)Co(CO)_2$ and said tri-osmium heteronuclear metal carbonyl produced comprises at least one of $H_2(\eta^5-C_5H_5)CoOs_3(CO)_{10}$, $H_3(\eta^5-C_5H_5)CoOs_3(CO)_9$, and $H_4(\eta^5-C_5H_5)CoOs_3(CO)_9$.

26. A process according to claim 25 wherein said reaction mixture comprises said $(\eta^5-C_5H_5)Co(CO)_2$ and said $H_2Os_3(CO)_{10}$ in a molar ratio of at least 1:1 and a non-polar solvent in which said cobalt said tri-osmium compounds are soluble, said reaction mixture being established at a temperature in the range of about 80° to about 120° C. and said gaseous hydrogen being bubbled through said reaction mixture.

27. A process according to claim 26 wherein said reaction mixture comprises about 5 moles of said $(\eta^5-C_5H_5)Co(CO)_2$ per mole of said $H_2Os_3(CO)_{10}$.

28. A process according to claim 26 wherein said solvent is an aromatic solvent.

29. A process according to claim 28 wherein said solvent is toluene.

30. A process according to claim 26 wherein said reaction mixture is established at a temperature of about 90° C.

31. A process according to claim 26 wherein said reaction mixture is chromatographed on silica gel using a hexane/benzene liquid phase to separate the products of said reaction.

32. A process according to claim 2 wherein said electron deficient carbonyl is $(\eta^5-C_5H_5)Rh(CO)_2$ and said tri-osmium heteronuclear metal carbonyl produced is $H_2(\eta^5-C_5H_5)RhOs_3(CO)_{10}$.

33. A process according to claim 32 wherein said reaction mixture comprises said $(\eta^5-C_5H_5)Rh(CO)_2$ and said $H_2Os_3(CO)_{10}$ in a molar ratio of at least about 1:1 and a non-polar solvent in which said rhodium and tri-osmium compounds are soluble, said reaction mixture being established at a temperature in the range of about 80° to about 120° C. and said gaseous hydrogen being bubbled through said reaction mixture.

34. A process according to claim 33 wherein said reaction mixture comprises about 5 moles of said $(\eta^5\text{-}C_5H_5)Rh(CO)_2$ per mole of said $H_2Os_3(CO)_{10}$.

35. A process according to claim 33 wherein said solvent is an aromatic solvent.

36. A process according to claim 35 wherein said solvent is toluene.

37. A process according to claim 33 wherein said reaction mixture is established at a temperature of about 90° C.

38. A process according to claim 33 wherein said reaction mixture is chromatographed on silica gel using a hexane/benzene liquid phase to separate the products of said reaction.

39. A process for preparing $H_4(\eta^5\text{-}C_5H_5)CoOs_3(CO)_9$ in which $H_3(\eta^5\text{-}C_5H_5)CoOs_3(CO)_9$ is dissolved in a non-polar solvent and gaseous hydrogen is passed through the resulting solution.

40. A process according to claim 39 wherein said solvent is toluene at a temperature of about 90° C.

* * * * *